(12) United States Patent
Yu et al.

(10) Patent No.: US 11,667,893 B2
(45) Date of Patent: Jun. 6, 2023

(54) METHODS FOR ESTABLISHING COLORECTAL CANCER P73 REPORTER GENE CELL LINE

(71) Applicant: Guangdong Medical University, Dongguan (CN)

(72) Inventors: Hongbing Yu, Dongguan (CN); Xin Liu, Dongguan (CN); Cuifang Han, Dongguan (CN)

(73) Assignee: Guangdong Medical University, Dongguan (CN)

( * ) Notice: Subject to any disclaimer, the term of this patent is extended or adjusted under 35 U.S.C. 154(b) by 727 days.

(21) Appl. No.: 16/680,920

(22) Filed: Nov. 12, 2019

(65) Prior Publication Data
US 2020/0208118 A1  Jul. 2, 2020

(30) Foreign Application Priority Data

Jan. 2, 2019  (CN) .......................... 201910002839.1

(51) Int. Cl.
| | | |
|---|---|---|
| C07H 21/02 | (2006.01) | |
| C07H 21/04 | (2006.01) | |
| C12N 5/09 | (2010.01) | |
| C12N 15/85 | (2006.01) | |
| C12N 5/071 | (2010.01) | |
| G01N 33/50 | (2006.01) | |

(52) U.S. Cl.
CPC ......... *C12N 5/0693* (2013.01); *C12N 5/0679* (2013.01); *C12N 15/85* (2013.01); *G01N 33/5011* (2013.01); *G01N 33/5044* (2013.01); *C12N 2310/20* (2017.05); *C12N 2320/10* (2013.01); *C12N 2800/107* (2013.01); *G01N 2500/02* (2013.01); *G01N 2500/10* (2013.01)

(58) Field of Classification Search
CPC ........................... C12N 15/85; C12N 2310/20
See application file for complete search history.

*Primary Examiner* — Amy H Bowman
(74) *Attorney, Agent, or Firm* — Dragon Sun Law Firm, PC; Nathaniel Perkins

(57) ABSTRACT

The present invention discloses a method for establishing a colorectal cancer p73 reporter gene cell line, specifically including: first designing a site-specific sgRNA sequence of a p73 gene and cloning same into a plasmid PX459; integrating a homologous recombination sequence of the p73 gene and a green fluorescent protein DNA fragment (EGFP), and transforming the plasmid and the integrated fragment together into a colorectal cancer cell line HCT116 by electroporation; performing signal cell screening through a flow cytometer to obtain EGFP-expressing cells, and amplifying a monoclonal cell line; and identifying a positive p73 reporter gene cell line through PCR identification and Western blot, among screened EGFP-expressing cell lines. The colorectal cancer cell line p73 gene and the EGFP are co-expressed, and the expression level of the EGFP is highly consistent with that of the p73 gene. Therefore, the expression level of the p73 gene can be accurately determined by detecting changes in the expression level of the EGFP. The method for establishing the cell line in the present invention is simple, easy to implement, high in efficiency and precise in gene site positioning.

1 Claim, 3 Drawing Sheets
Specification includes a Sequence Listing.

SEQUENCE LISTING

```
<160> NUMBER OF SEQ ID NOS: 6

<210> SEQ ID NO 1
<211> LENGTH: 20
<212> TYPE: DNA
<213> ORGANISM: artificial sequence
<220> FEATURE:
<223> OTHER INFORMATION: p73-sgRNA1

<400> SEQUENCE: 1
cggaggccga gatccactga                                                  20

<210> SEQ ID NO 2
<211> LENGTH: 1838
<212> TYPE: DNA
<213> ORGANISM: artificial sequence
<220> FEATURE:
<223> OTHER INFORMATION: L-EGFP-R

<400> SEQUENCE: 2
caggccagga gtgactctgg tgggctctcc ccctccccg tctcctgcct actctggttg      60
ggggtgtagg ggccagggtg tggtgtggcc agacctccag gcccagggcg accccccctg    120
ctctccctgc tccactgccc cctgcccta atgcgccggc ctctcgcagg acctggggc      180 cctgaagatc cccgagcagt accgcatgac catctggcgg ggcctgcagg acctgaagca    240
gggccacgac tacagcaccg cgcagcagct gctccgctct agcaacgcgg ccaccatctc    300
catcggcggc tcaggggaac tgcagcgcca gcgggtcatg gaggccgtgc acttccgcgt    360
```

```
gcgccacacc atcaccatcc ccaaccgcgg cggcccaggc ggcggccctg acgagtgggc    420
ggacttcggc ttcgacctgc ccgactgcaa ggcccgcaag cagcccatca aggaggagtt    480
cacggaggcc gagatccacg tgagcaaggg cgaggagctg ttcaccgggg tggtgcccat    540
cctggtcgag ctggacggcg acgtaaacgg ccacaagttc agcgtgtccg gcgagggcga    600
gggcgatgcc acctacggca agctgaccct gaagttcatc tgcaccaccg gcaagctgcc    660
cgtgccctgg cccaccctcg tgaccaccct gacctacggc gtgcagtgct tcagccgcta    720
ccccgaccac atgaagcagc acgacttctt caagtccgcc atgcccgaag gctacgtcca    780
ggagcgcacc atcttcttca aggacgacgg caactacaag acccgcgccg aggtgaagtt    840
cgagggcgac accctggtga accgcatcga gctgaagggc atcgacttca aggaggacgg    900
caacatcctg gggcacaagc tggagtacaa ctacaacagc cacaacgtct atatcatggc    960
cgacaagcag aagaacggca tcaaggtgaa cttcaagatc cgccacaaca tcgaggacgg   1020
cagcgtgcag ctcgccgacc actaccagca gaacaccccc atcggcgacg gccccgtgct   1080
gctgcccgac aaccactacc tgagcaccca gtccgccctg agcaaagacc ccaacgagaa   1140
gcgcgatcac atggtcctgc tggagttcgt gaccgccgcc gggatcactc tcggcatgga   1200
cgagctgtac aagggcggag agggcagagg aagtctgcta acatgcggtg acgtcgagga   1260
gaatcctggc ccaggcggag gtaagcctat ccctaaccct ctcctcggtc tcgattctac   1320
ggggcctcgc ctggctgcag cctgcgccac cgcccagaga cccaagctgc ctcccctctc   1380
cttcctgtgt gtccaaaact gcctcaggag gcaggacctt cgggctgtgc cggggaaag    1440 gcaaggtccg gcccatcccc aggcacctca caggcccag gaaaggccca gccaccgaag    1500
ccgcctgtgg acagcctgag tcacctgcag aaccttctgg agctgcccta gtgctgggct   1560
tgtggggcgg gggctggccc actctcagcc ctgccactgc cccggcgtgc tccatggcag   1620
gcgtgggtgg ggaccgcagc gtcggctccg acttccaggc ttcatcctag agactgtcat   1680
ctcccaacca ggcgaggtcc ttccaaagga aaggatcctc tttgctgatg gactgccaaa   1740
aagtattttg cgacatcttt tggttctgga tagtagtgag cagccaagtg actgtgtctg   1800
aaacaccagt gtattttcag ggaatgtccc taactgcg                           1838

<210> SEQ ID NO 3
<211> LENGTH: 25
<212> TYPE: DNA
<213> ORGANISM: artificial sequence
<220> FEATURE:
<223> OTHER INFORMATION: F-GT

<400> SEQUENCE: 3 ggggggccctg aagatccccg agcag                                         25

<210> SEQ ID NO 4
<211> LENGTH: 24
<212> TYPE: DNA
<213> ORGANISM: artificial sequence
<220> FEATURE:
<223> OTHER INFORMATION: R-GT

<400> SEQUENCE: 4
ccgaggagag ggttagggat aggc                                           24

<210> SEQ ID NO 5
<211> LENGTH: 25
<212> TYPE: DNA
```

```
<213> ORGANISM: artificial sequence
<220> FEATURE:
<223> OTHER INFORMATION: F-WT

<400> SEQUENCE: 5
gggggccctg aagatccccg agcag                                              25

<210> SEQ ID NO 6
<211> LENGTH: 20
<212> TYPE: DNA
<213> ORGANISM: artificial sequence
<220> FEATURE:
<223> OTHER INFORMATION: R-WT

<400> SEQUENCE: 6
gctgcagcca ggcgaggccc                                                    20
```

METHODS FOR ESTABLISHING COLORECTAL CANCER P73 REPORTER GENE CELL LINE

REFERENCE TO RELATED APPLICATION

This application claims the benefits of the filing dates of Chinese patent application Serial No. 201910002839.1 filed on Jan. 2, 2019, entitled "METHOD FOR ESTABLISHING COLORECTAL CANCER p73 REPORTER GENE CELL LINE". The teachings of the entire referenced application are incorporated herein by reference. A copy of the newly amended "Sequence Listing" in computer readable from (CRF) has been submitted via EFS-Web. Such "Sequence Listing" as part of the disclosure is an amendment specifically directing its entry into the application. The newly amended "Sequence Listing" includes no new matter and support for the amendment in the application is filed as required by 37 CFR1.825 and the "Legal Framework". The new Sequence Listing text file is named "SequenceListingAmendment01272020", which is created on Jan. 27, 2020.

TECHNICAL FIELD

The present invention relates to the technical field of biology, and in particular, to colorectal cancer p73 reporter gene cell lines and methods for establishing same.

BACKGROUND

Reporter gene is an important tool in the field of molecular biology research and is generally used to mark a target gene to be researched, so that the expression level of the reporter gene is consistent with the expression level of the target gene, and thus the expression regulation of the target gene can be observed by expressing the reporter gene. The reporter gene has the advantages of convenience, reliability, high sensitivity, high flux detection and the like. At present, the commonly used reporter genes include β-galactosidase, luciferase, fluorescent protein and the like. As non-toxic and harmless detection tools, luciferase and fluorescent protein occupy a dominant position in the detection of cellular gene expression.

CRISPR-Cas is an adaptive immune system consisting of Clustered Regularly Interspaced Short Palindromic Repeat (CRISPR) sequences of bacteria and archaea, and is used for resisting invasion of exogenous genetic materials. There is a plurality of types of Cas proteins, which have endonuclease activity. The CRISPR-Cas systems include three categories, among which CRISPR-cas9 is the most deeply researched and most maturely applied category at present; the system has the advantages of ease of operation, high flexibility in action site selection, high activity, and the like. Under the guidance of human-designed sgRNA, the expressed Cas protein having the endonuclease activity may move towards the position of a gene target, and finally functions in combination with the gene target. When the integrity of a cell genome is damaged by Cas proteinase, a self-repairing system of the cell is activated, and in the presence of an exogenous target gene with a genome homologous fragment, the cell may repair its own genome in a homologous recombination manner with a certain probability, thereby implementing insertion of an exogenous gene.

A p73 gene (Homo sapiens tumor protein p73, TP73, GenBank ID: NG_017035.2) is a member of a p53 transcription factor family, and the p53 gene family further includes a p53 gene and a p63 gene. The p73 gene is a false positive cDNA clone incidentally found by researchers such as Kag had by performing hybridization screening on cDNA libraries of COS cells using degenerate oligonucleotide probes corresponding to the IRS-1 junction area when screening insulin-mediated cell signaling factors in 1997, and the sequence thereof is highly homologous to that of the p53 gene (Nature, 1997.389:191-194.).The proteins encoded by the p73 gene and the p53 gene have little difference in structure and function. The p73 gene can activate the target gene of p53, induce apoptosis, and inhibit cell growth in the same manner as the P53 gene (*Clinical Cancer Research*, 2002.8(1): 165-170.). Many researchers have suggested that the p73 gene may be involved in the formation of some tumors through activation or overexpression of its silent genes (Cell Biology, 2007.178:283-296.). In recent years, related researches have shown that the expression level of the p73 gene is associated with tumor differentiation, and the lower the differentiation of cancer cells, the higher the expression of this gene (*Molecular Cancer Research*, 2016.14(1):56-65.). In summary, the detection of the p73 gene has important reference significance for the diagnosis, staging and prognosis of tumors.

This research relates to the field of colorectal cancer p73 reporter genes, and a cell line of colorectal cancer p73 reporter genes with Enhanced Green Fluorescent Protein (EGFP) was constructed using CRISPR-Cas9 technology, thereby providing a favorable tool for the research of the p73 gene and its signaling pathway, research on the pathogenesis of related diseases, drug screening and evaluation.

SUMMARY

The first purpose of the present invention is to provide a colorectal cancer p73 reporter gene cell line, where the p73 gene of the cell line is linked to a downstream reporter gene through a 2A peptide to implement co-expression.

Preferably, the colorectal cancer cell is HCT116, Caco-2, SW480, SW620, LOVO, HT29 or DLD-1, more preferably, HCT116.

Preferably, the reporter gene is GFP, EGFP, Luciferase or RFP.

The second purpose of the present invention is to provide a method for establishing a colorectal cancer p73 reporter gene cell line, including the following steps:

step 1: designing and evaluating a downstream site-specific p73-sgRNA sequence of a p73 gene;

step 2: constructing a pX459/p73-sgRNA plasmid;

step 3: integrating a homologous recombination sequence of the p73 gene and an EGFP fragment;

step 4: transforming the plasmid pX459/p73-sgRNA and the green fluorescent protein integrated fragment together into a colorectal cancer cell line HCT116 by electroporation with a ratio of 1:1;

step 5: performing single cell screening through a flow cytometer to obtain EGFP-expressing cells, and amplifying a monoclonal cell line; and step 6: further identifying a positive p73 reporter gene cell line through genome PCR and Western blot, among the screened EGFP-expressing cells.

Preferably, in step 1, the p73-sgRNA sequence is designed and screened, and the sequence of the p73-sgRNA is as set forth in SEQ ID NO. 1.

Preferably, in step 2, the method for constructing a pX459/P73-sgRNA plasmid includes the following step: directly obtaining the plasmid pX459/p73-sgRNA of a correct sgRNA sequence after synthesizing by a biological company according to the sequence of the p73-sgRNA.

Preferably, in step 3, the method for integrating a homologous recombination sequence of the p73 gene and an EGFP fragment includes the following step: directly obtaining a correct integrated fragment L-EGFP-R after synthesizing by the biological company according to the homologous recombination sequence of the p73 gene and an EGFP sequence.

Preferably, the sequence of the fragment L-EGFP-R is as set forth in SEQ ID NO. 2.

The third purpose of the present invention is to provide an application of the colorectal cancer p73 reporter gene cell line in tumor cell occurrence, development or energy metabolism research.

Preferably, the tumor is colorectal cancer.

The fourth purpose of the present invention is to provide an application of the colorectal cancer p73 reporter gene cell line in a cell model.

Preferably, the cell model is a tumor cell model, more preferably, a colorectal cancer cell model.

The fifth purpose of the present invention is to provide an application of the colorectal cancer p73 reporter gene cell line in the research of a p73 gene.

The sixth purpose of the present invention is to provide an application of the colorectal cancer p73 reporter gene cell line in screening molecules or drugs for regulating and controlling the p73 gene change.

Preferably, the drugs are anticancer drugs, more preferably, the drugs are anti-colorectal cancer drugs.

On the basis of conforming to common general knowledge in the art, the preferred conditions above may be combined with one another to obtain specific implementation modes.

Unless specifically stated otherwise, the technical and scientific terms used in the present invention have the same meaning as understood by persons skilled in the art. The naming method and the described experimental method used in the present invention are widely known and are commonly used in the field.

Compared with the prior art, the present invention has the following beneficial effects:

(1) In the present invention, p73-sgRNA capable of efficiently targeting and binding to a target site may be determined by means of hierarchical screening, and the constructed pX459/p73-sgRNA plasmids and the integrated EGFP fragments are directly subjected to electroporation together with a certain ratio to be transformed into a colorectal cancer cell line HCT116, so that the purposes of rapidly detecting the colorectal cancer p73 reporter gene cell having EGFP expression and establishing a stable cell line subsequently are ensured.

(2) The method in the present invention is simple, feasible and efficient. The well-designed and screened reporter gene is inserted into a site, and the gene site is precisely positioned by using sgRNA so as to quickly obtain the stable cell line for the target gene to be inserted, and thus, the method has the advantages of less time consumption and high success rate. The result shows that the EGFP knock-in efficiency reaches 7-8%. In this experiment, 7-10 strains may be screened per 96-well plate, which is significantly higher than the knock-in efficiency of generally 1% in this field. Moreover, after stable passage of 30 generations of the cell line, sequencing shows that the gene knock-in sequence still keeps genetic stability.

(3) The p73 gene and the reporter gene EGFP are linked through a 2A self-cleaving peptide to construct an operon. The self-cleaving function of the 2A peptide ensures that the p73 gene and the EGFP may be co-expressed in cells and do not interfere with each other, and thus, the tracing effect of the reporter gene on the p73 gene is achieved.

(4) The cell line in the present invention can be monitored in real time, is simple and visible, greatly promotes the research on related drug metabolism evaluation and related gene functions, and has clinical popularization potential and application value.

DETAILED DESCRIPTION

The present invention will be further described below in specific embodiments, so that persons skilled in the art can better understand the present invention and implement same. However, the present invention is not limited to the embodiments.

Unless otherwise specified, the experimental methods used in the following embodiments are all conventional methods, and the used materials and reagents can be obtained by commercial approaches.

Embodiment 1

Establishment of a Colorectal Cancer p73 Reporter Gene Cell Line

At step 1, an appropriate p73-sgRNA sequence is designed and evaluated;

an sgRNA sequence is obtained through screening and evaluation, and is shown as follows:

p73-sgRNA: CGGAGGCCGAGATCCACTGA (>chr1: 3733060-3733079), as set forth in SEQ ID NO. 1.

At step 2, a pX459-sgRNA plasmid is constructed, including the following step:

directly obtaining the plasmid pX459/p73-sgRNA of a correct sgRNA sequence after synthesizing by a biological company according to the sequence of the p73-sgRNA.

Figure 1:
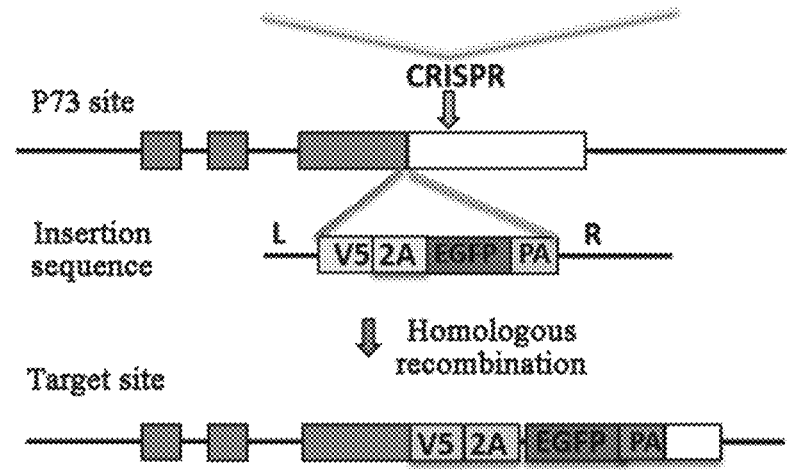
FIG. 1 is a schematic diagram of a green fluorescent protein target gene knock-in mechanism.

At step 3, an L-EGFP-R fragment is obtained by integration, including the followings step:

directly obtaining a correct integrated fragment L-EGFP-R after synthesizing by the biological company according to a homologous arm of the p73 gene and an EGFP sequence. The sequence is as set forth in SEQ ID NO. 2, and the construction process is shown in FIG. 1.

At step 4, a colorectal cancer p73 reporter gene cell line having green fluorescence is screened, including the following step:

transforming the plasmid pX459/p73-sgRNA and the green fluorescent protein integrated fragment together into a colorectal cancer cell line HCT116 by electroporation with a ratio of 1:1.

Figure 2:
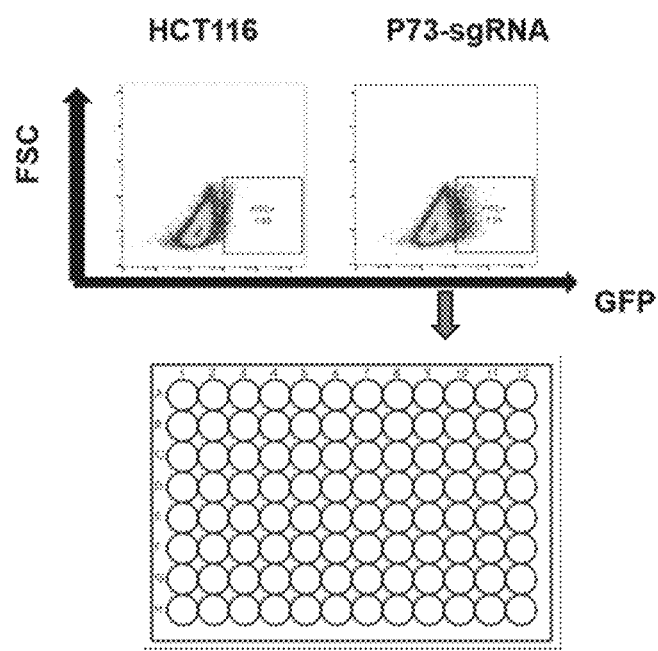
FIG. 2 shows screening of single cell clones expressed by green fluorescent proteins through a flow cytometer.

First, single cell screening is performed using 96-well plates in a flow cytometer (see FIG. 2), and 7-10 cell strains having EGFP expression may be obtained by each 96-well plate. The EGFP knock-in efficiency reaches 7-8%, which is significantly higher than the knock-in efficiency of generally 1% in this field.

Figure 3:
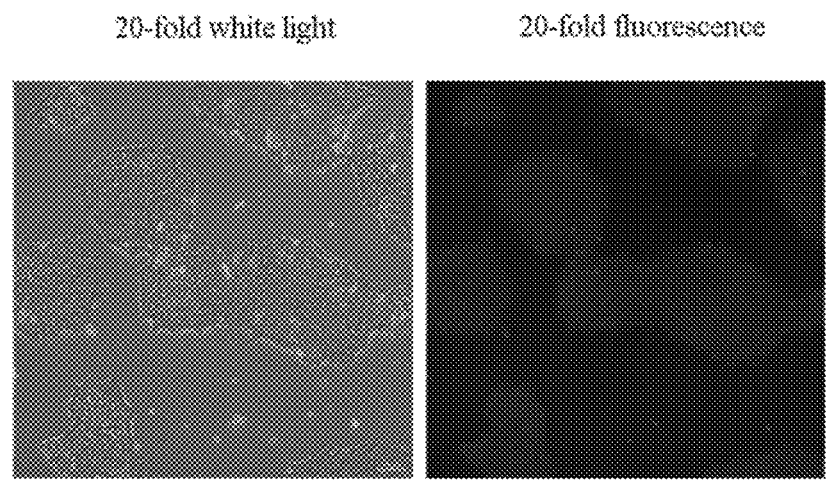
FIG. 3 shows a green fluorescent protein expressed by a screened positive p73 reporter gene cell line.

A selected monoclonal cell line is amplified and cultured (see FIG. 3). A genome DNA of cells having EGFP expression is extracted and obtained. Genome PCR is performed, and if positive amplification is obtained, it indicates that the insertion is successful, and a p73 reporter gene cell line is obtained. The primer sequences for PCR identification are as follows:

```
Forward primer F-GT: GGGGGCCCTGAAGATCCCCGAGCAG,
as set forth in SEQ ID NO. 3; and Reverse primer R-GT: CCGAGGAGAGGGTTAGGGATAGGC,
as set forth in SEQ ID NO. 4.
```

Wild type cells are also subjected to genome PCR, and the primer sequences for PCR identification are as follows:

```
Forward primer F-WT: GGGGGCCCTGAAGATCCCCGAGCAG,
as set forth in SEQ ID NO. 5; and Reverse primer R-WT: GCTGCAGCCAGGCGAGGCCC,
as set forth in SEQ ID NO. 6.
```

Figure 4:
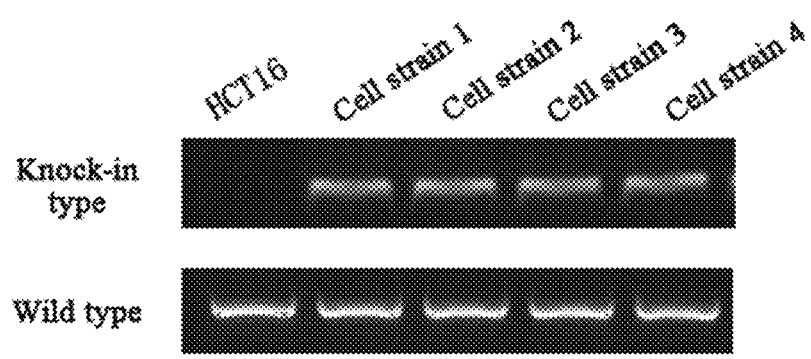
FIG. 4 shows identification of the p73 reporter gene cell line through PCR.

The comparison result of PCR identification is shown in FIG. 4, and four p73 reporter gene cell lines are obtained.

Figure 5:
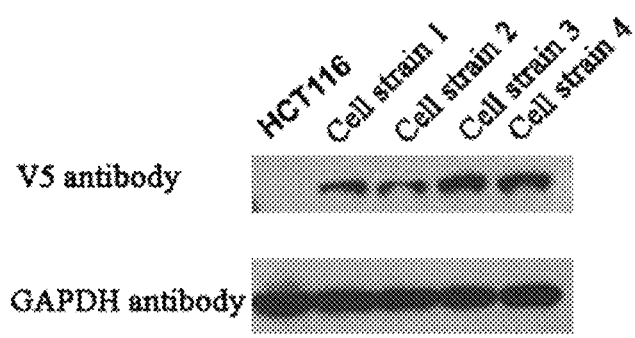
FIG. 5 shows identification of the p73 reporter gene cell line through Western blot.

Finally, a positive p73 reporter gene cell line is further identified through genome PCR and Western blot, among the screened EGFP-expressing cells. The identification result is shown in FIG. 5, and finally, four p73 reporter gene cell lines are obtained.

After stable passage of 30 generations of the p73 reporter gene cell line, sequencing shows that the gene knock-in sequence still keeps genetic stability.

Embodiment 2

Functional Verification of a Colorectal Cancer p73 Reporter Gene Cell Line

Figure 6:
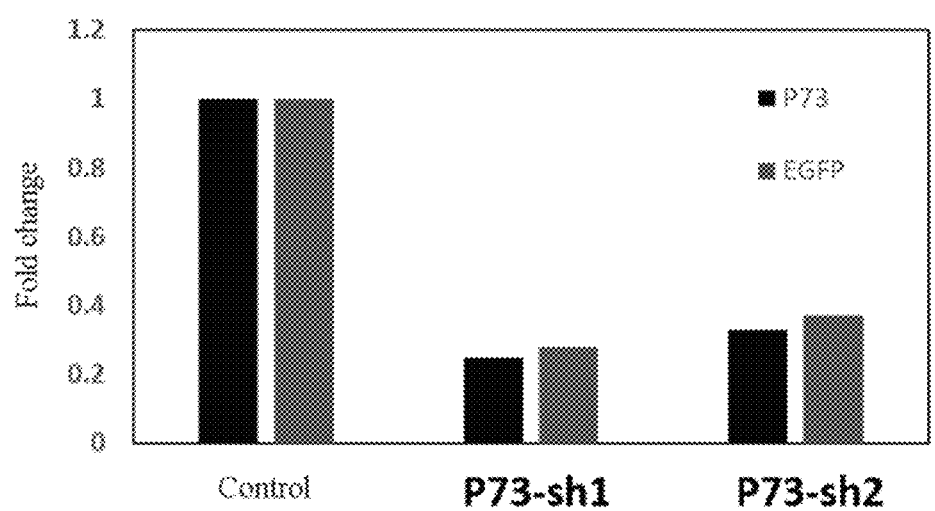
FIG. 6 shows knockdown of co-expression of p73 and EGFP by shRNA.

Two different specific targeted p73 gene small-molecule interference RNAs are designed, i.e., shRAN-1 and shRAN-2 as shown in FIG. 6, which are respectively transfected into an p73 reporter cell line. After 72 hours, according to transcriptional level analysis, it shows that compared with non-knock-down control, the two specific small-molecule interference RNAs effectively reduce the expression level of the p73 gene (about 70-80% is knocked down). Moreover, the expression of the EGFP gene is also correspondingly reduced by 70-80% along with the knockdown of the p73 gene. The experimental result proves from a molecular level that the reporter gene EGFP and the p73 gene in the colorectal cancer p73 reporter gene cell line constructed in the present invention can be synchronously co-expressed, are synchronously inhibited by shRNA, and can be used for inhibition or over-expression tracing of the p73 gene.

Finally, it should be noted that the aforementioned embodiments are only used for describing the technical solutions of the present invention rather than limiting the scope of protection of the present invention. Although the present invention has been described in detail with reference to the preferred embodiments, persons skilled in the art should understand that the technical solutions of the present invention may be modified or equivalently replaced without departing from the essence and scope of the technical solutions of the present invention.

The invention claimed is:

1. A method for establishing a colorectal cancer p73 reporter gene cell line, the method comprising the following steps:

step 1: obtaining a downstream site-specific p73-sgRNA sequence of a p73 gene, wherein the sequence of the p73-sgRNA is as set forth in SEQ ID NO. 1;

step 2: constructing a pX459/p73-sgRNA plasmid;

step 3: integrating a homologous recombination sequence of the p73 gene and an EGFP fragment;

step 4: transforming the plasmid pX459/p73-sgRNA and the green fluorescent protein integrated fragment together into a colorectal cancer cell line HCT116 by electroporation with a ratio of 1:1;

step 5: performing single cell screening through a flow cytometer to obtain EGFP-expressing cells, and amplifying a monoclonal cell line; and step 6: further identifying a positive p73 reporter gene cell line through genome PCR and Western blot, among the screened EGFP-expressing cells;

wherein in step 2, the method for constructing a pX459/p73-sgRNA plasmid comprises the following step: directly obtaining the plasmid pX459/p73-sgRNA with a correct ssRNA sequence after synthesizing by a biological company according to the sequence of the p73-sgRNA; in step 3, the method for integrating a homologous recombination sequence of the p73 gene and an EGFP fragment comprises the following step: directly obtaining a correct integrated fragment L-EGFP-R after synthesizing by the biological company according to the homologous recombination sequence of the p73 gene and an EGFP sequence; and the sequence of the fragment L-EGFP-R is as set forth in SEQ ID NO. 2.

* * * * *